(12) United States Patent
Persson et al.

(10) Patent No.: US 6,854,600 B1
(45) Date of Patent: Feb. 15, 2005

(54) USE OF MOISTURE IMPERVIOUS PACKAGING UNITS AND PACKAGE FOR ABSORBENT ARTICLES COMPRISING MOISTURE-SENSITIVE ADDITIVES

(75) Inventors: Charlotte Persson, Göteborg (SE); Håkan Persson, Göteborg (SE)

(73) Assignee: SCA Hygiene Products AB, Gothenburg (SE)

(*) Notice: Subject to any disclaimer, the term of this patent is extended or adjusted under 35 U.S.C. 154(b) by 181 days.

(21) Appl. No.: 10/018,577

(22) PCT Filed: Jun. 9, 2000

(86) PCT No.: PCT/SE00/01207
§ 371 (c)(1), (2), (4) Date: Aug. 30, 2002

(87) PCT Pub. No.: WO00/76878
PCT Pub. Date: Dec. 21, 2000

(30) Foreign Application Priority Data
Jun. 11, 1999 (SE) .............................. 9902207

(51) Int. Cl.[7] .............................................. B65D 73/00
(52) U.S. Cl. .................... 206/494; 206/204; 53/431
(58) Field of Search ................. 206/204, 484, 206/494, 459.1; 53/428, 431, 467, 473; 424/400, 404; 428/34.9, 35.2; 604/358, 385.01, 385.02

(56) References Cited

U.S. PATENT DOCUMENTS

| | | | |
|---|---|---|---|
| 5,443,161 A | 8/1995 | Jonese | |
| 5,833,070 A | 11/1998 | Mizuno et al. | |
| 5,875,891 A | * 3/1999 | Snell | ...................... 206/315.9 |
| 5,988,368 A | * 11/1999 | Kitamura et al. | ........... 206/204 |
| 6,119,853 A | * 9/2000 | Garrill et al. | ................ 206/204 |

FOREIGN PATENT DOCUMENTS

| | | |
|---|---|---|
| EP | 0613824 A3 | 9/1994 |
| EP | 0773102 A1 | 5/1997 |
| SE | 9502588-8 | 7/1995 |
| SE | 9703669-3 | 10/1997 |
| SE | 9801951-6 | 6/1998 |
| SE | 9804390-4 | 10/1998 |
| WO | 92/13577 | 8/1992 |
| WO | 97/46188 | 12/1997 |
| WO | 97/46190 | 12/1997 |
| WO | 97/46192 | 12/1997 |
| WO | 97/46193 | 12/1997 |
| WO | 97/46195 | 12/1997 |
| WO | 97/46196 | 12/1997 |
| WO | 98/17239 | 4/1998 |
| WO | WO 99/17813 | 5/1999 |

* cited by examiner

*Primary Examiner*—Luan K. Bui
(74) *Attorney, Agent, or Firm*—Burns, Doane, Swecker & Mathis, L.L.P.

(57) ABSTRACT

Active additives in absorbent articles, such as sanitary napkins, panty liners, tampons, incontinence protectors and diapers have been found to lose their properties due to taking-up moisture during storage and transportation for instance, when conventional packaging materials are used. The invention relates to the use of a moisture impervious film material for packaging an absorbent article comprising one or more active moisture-sensitive additives. Packaging is effected in film material that has low vapor and gas permeability and in packaging unites that have tight joins or seams.

15 Claims, 3 Drawing Sheets

4-side sealing

Folded film with 3-side sealing

Flow-packed with fin sealing 4-side sealing

Folded film with 3-side sealing

Flow-packed with fin sealing

USE OF MOISTURE IMPERVIOUS PACKAGING UNITS AND PACKAGE FOR ABSORBENT ARTICLES COMPRISING MOISTURE-SENSITIVE ADDITIVES

FIELD OF INVENTION

The present invention relates to the use of moisture impervious packaging units for absorbent articles, such as sanitary napkins, panty liners, tampons, incontinence protectors and diapers, that comprise one or more active, moisture-sensitive additives or substances. The packaging unit is comprised of film material that has low vapour and gas permeability and tight joins.

BACKGROUND OF THE INVENTION

Absorbent articles, such as sanitary napkins, diapers, incontinence protectors, panty liners and tampons have consistently been packaged in open packages into which air can enter freely. Packaging of this nature has many advantages. Handling with respect to manufacture and also with respect to the individual consumer is facilitated by the fact that the package containing the absorbent article can be compressed (air can leave the package freely), and the package can also be easily opened. It is also difficult from a purely technical aspect to produce tight joins at present day production rates.

However, it is becoming more common to include different active additives in absorbent products for different reasons. Examples in this respect are odour-inhibiting additives or deodorants, such as zeolites and silica for example, as described, inter alia, in WO 97/46188, WO 97/46190, WO 97146192, WO 97/46193, WO 97/46195 and WO 97/46196. These additives are intended to act essentially in the product. Another example is the addition to diapers of softeners, e.g. lotions, which shall be transferred from the product to the wearer's skin. A further example is the addition of lactobacilli with the intention of inhibiting bacteria in the product, or for transfer to the wearer and thereby enhance defence against undesired bacteria. The addition of lactobacilli and their favourable effects is also mentioned in, inter alia, SE 9703669-3, SE 9502588-8, WO 92/13577, SE 9801951-6 and SE 9804390-4.

The aforesaid additives often loose some of their properties or effectiveness at high moisture contents. This problem is thus new in the field of absorbent products. The odour-inhibiting capacity of zeolites is reduced when they become saturated with water. This is mentioned, inter alia, in WO 98/17239. One problem with lactobacilli in absorbent products resides in their rapid demise when exposed to ambient moisture and temperature above a certain threshold; see FIG. 3. Thus, in normal surroundings such as in transportation and during storage, for instance, the absorbent articles will be subjected to such conditions as to render the death of the lactobacilli present unavoidable (see FIG. 1) when the articles are packaged in accordance with known technology. Survival of lactobacilli can be achieved by bringing them into a rest state. This state can be achieved either by freezing or drying the lactobacilli, or by a combination of these processes, i.e. so called freeze-drying. In order to make possible the use of conventional absorbent product distribution and sales channels, drying of the lactobacilli and retention of this dryness is preferred to freezing. When the product, or article, is applied to the body, the moisture and temperature conditions that then prevail will be optimal for reactivation of the lactic acid bacteria.

However, it may be difficult to retain dryness when storing in a humid atmosphere. This applies particularly to absorbent products, as it lies in the nature of the product to absorb moisture from the surrounding atmosphere. It is therefore particularly important to protect absorbent products that contain lactobacilli against high humidities. The packages used at present for packaging absorbent articles cannot be considered to satisfy the need for such protection, partly because the material used is moisture permeable and secondly because the packaging joins or seams are not tight. Single-item packaging units for sanitary napkins and panty liners are often comprised of polypropylene or polyethylene plastic, which have a relatively high moisture permeability (see table 1, film 8), and the packages are also often provided with an unsealed opening in the centre of the package, so that air is able to pass freely into and out of the package and therewith permit a certain degree of compression. External wrappers or bags are also often perforated to facilitate opening of the package.

U.S. Pat. No. 5,833,070 refers to a stretched film of polychlorotrifluoroethylene, a method for its production, and a product package, in which the film is used. The film must at least partly comprise trifluoroethylene. The film can be used to pack some products in a moisture impermeable way, such as preferably an electro-luminiscent means. Thus, this film is stretched, which leads to it being stiff, fragile and rustle. Accordingly, it is not suitable as a package film for hygiene articles for some reasons. A film for hygiene articles should be silent and smooth to be experienced as discrete by the consumer. A film for hygiene article applications should also be possible to fold, which makes a stiff film unsuitable. Further, the air in the product should be pressed out in the same step as the packaging, which makes a stiff, blister-package like film inadequate.

EP-A1-0773102 refers to a multi-layer laminate and its use. One of the layers must at least partly comprise an ethylene-/cycloolephine-copolymer, and one layer must be a polymer layer. Polyethylene, polypropylene and vinyl are mentioned as possible materials. The thickness of the layers can be 1 $\mu$m–10 mm. This laminate can be used as a moisture protection for drugs and food. The laminate is for instance suitable for use as a PTP (press through pack) or as a blister package. Those types of packages are not suitable for absorbent products, for the reasons discussed above.

Further, EP-A2-0613824 discloses a moisture tissue-containing package, having the object to retain the moisture in a package. The film disclosed here is too thick for use in relation to absorbent articles. U.S. Pat. No. 5,443,161 describes a moisture impermeable "baby-care"-kit, in which the package consists of a polypropylene layer, having a thickness of 2 mm.

In summary, there is thus a need to package absorbent articles that contain moisture-sensitive additives in a manner, which will ensure that these additives will not be harmed or destroyed and which will also ensure that the quality of the product is retained.

OBJECT OF THE INVENTION

Accordingly, the object of the present invention is to provide protection against the effect of ambient moisture from the time of packaging an absorbent article to the time when it is used, so as to allow the active additive to retain its properties in the absorbent article during storage and when the absorbent article is used.

SUMMARY OF THE INVENTION

The invention relates to the use of an essentially tight film material that has a highest WVTR (Water Vapour Transmission Rate) of 6 g/m²/calendar day in accordance with ASTME 398-83 at 87.8° C. (100° F.) and 90% relative humidity for packaging an absorbent article that comprise one or more moisture sensitive additives.

DETAILED DESCRIPTION OF THE INVENTION

By an "essentially impermeable" film material is meant a material whose impermeability is so high that a package comprised of said material will not allow more moisture to enter than that at which the active moisture-sensitive additive present in the package will essentially retain their properties despite this uptake of moisture. This means that the packaging unit may have a highest WVTR (Water Vapour Transmission Rate) of 6 g/m²/calendar day according to ASTME 398-83 at 37.8° C. (100° F.) and 90% relative humidity, preferably at most 4 g/m²/calendar day, and more preferably at most 2 g/m²/calendar day and even more preferably at most 1 g/m²/calendar day. The material used will also preferably protect the moisture-sensitive additives in such a way that said additives will retain their effect for at least 9 months and preferably for 18 months after the packaging date.

By "film material" is meant film that is produced, at least partially, from one or more polymers suitable for use in accordance with the invention, such as PE (polyethylene), PP (polypropylene), PET (polyester), PA (polyamide), PETP, PVA (polyvinyl alcohol), or similar polymers, or aluminium foil, aluminium oxide or silicon oxide or the like, an example of these latter three materials being Techbarrier S, V, H, T, AT, NR, NY Mitsubishi, Helional WTY (Amcor Flexibles), VA 535670 (metallised PE/PET) (Nordenia), 4364 (Schur-Flexible), Coex HDPE Surlyn (Schur-Flexible), Coex Cheerios (Schur-Flexible).

The data and values mentioned in the aforegoing with respect to WVLR (Water Vapour Transmission Rate) correspond to unsaturated values in accordance with the standard ASTME 398-83, which is generally applied in this field and is known to the person skilled in this art.

By "absorbent article" is meant articles such as sanitary napkins, diapers, tampons, panty liners, incontinence protectors and similar products, that are partially comprised of absorbent material, for instance a cellulose material such as airlaid, LDA, chemical pulp or CTMP.

By "moisture-sensitive additives" is meant additives that are intended to contribute to the effect and function of the product in some way and whose properties may be impaired when they are exposed to moisture, e.g. in storage. Examples of such moisture-sensitive additives are odour-inhibiting additives, such as zeolites and silica, and lactobacilli.

In order to obtain an essentially impermeable packaging unit, the WVTR of the polymeric material used for packaging purposes will be at most 6 g/m²/24 h measured in accordance with ASTME 398-83 at 37.8° C. (100° F.) and 90% relative humidity, preferably at most 4 g/m²/24 h, and more preferably at most 2 g/m²/24 h and even more preferably at most 1 g/m²/24 h.

Polymeric material suitable for use as packaging unit is, e.g., PE (polyethylene), PP (polypropylene), PET (polyester), PA (polyamide), PETP, PVA (polyvinyl alcohol), or like polymeric material. Aluminium foil, aluminium oxide or silicon oxide, for instance, is used as supplementary sealing material. Examples of such materials are Techbarrier S, V, H, T, AT, NR, NY (Mitsubishi), Helional WTY (Amcor Flexibles), VA 535670 (metallised PE/PET) (Nordenia), 4364 (Schur-Flexible), Coex HDPE Surlyn (Schur-Flexible), Coex Cheerios (Schur-Flexible).

The films used will preferably have a thickness of 10–200 μm, preferably 20–100 μm.

The packaging material used is preferably comprised of several layers, where different layers may consist of different materials. The material intended to form a moisture barrier (impervious layer) is often expensive and there is preferably used the thinnest possible film with which the moisture blocking properties will nevertheless still be acceptable. In order to produce packaging material that has good wear strength and can be readily sealed, a less expensive material may be used as outer protective wear layers and/or as inner sealing layers. For instance, the packaging material may include an inner material that enables a good seal to be obtained, e.g. PE, PP, EVA, EEA or wax, an intermediate material that consists of the moisture-protective barrier material, the impervious layer, e.g. aluminium, aluminium oxide, silicon oxide or polyamide (nylon), and a somewhat stronger outer material that functions as barrier material, e.g. PETP, PE or PP. The packaging material may consist of one to ten layers of different materials.

In order to ensure that the packaging unit will prevent the ingress of moisture, it is also important that the package is completely closed with tight joins and seams so that the WVTR of the package will be at most 6 g/m²/24 h measured in accordance with ASTME 398-83 at 37.8° C. (100° F.) and 90% relative humidity, preferably at most 4 g/m²/24 h, and more preferably at most 2 g/m²/24 h and even more preferably at most 1 g/m²/24 h, even when measured across the joins and seams.

The impermeability of the joins and seams shall at least be equal to the impermeability of the film. Suitable sealing methods are, e.g., heat sealing, heat sealing at low temperatures, or cold scaling. The package may contain one or more articles.

Package sealing methods include heat sealing, heat sealing at low temperatures and cold sealing. In the case of cold sealing and heat sealing at low temperatures, a sealing layer, such as EVA, EEA or wax, is applied to the sealing side of the packaging unit. This sealing layer can be applied over the whole of the surface or solely where sealing shall occur, so-called border coating. In order to facilitate heat scaling, the films used as the impervious packaging layer and welding layer will normally include low density polyethylene (LDPE), optionally co-polymerised with butyl acrylate (EBA) or vinyl acetate (EVA). This enables heat sealing to be effected at high speeds. When packaging an article/articles, it is necessary to press the sealing material together around the product in the case of all sealing methods. This is achieved with the aid of cold, hot or slightly heated wheels or sealing jaws and must be effected at a pressure, and temperature and over a given time period that are appropriate for the material chosen and that will result in the intended joint tightness and joint strength.

The various layers may also be glued together.

The packaging unit shall be given the form of a bag and will preferably be easily opened without requiring the use of a tool to this end, for instance along a tear line. FIG. 2 shows alternative designs.

The size of the packaging unit will depend on the size of the product and whether the product is three-folded, two-folded or unfolded or folded in some other way when packaged. Folding of the product may be effected in different ways. For instance, a three-folded product may be folded so as to form three parts of identical sizes or so as to form three parts of different sizes. The size of a packaging unit according to the invention will be 77–140 mm (length of the packaging unit across the width of the product) and 75–310 mm (length of the packaging unit in the longitudinal direction of the product) in the case of napkin (including mini-napkin, standard napkin+super and night napkin); 72–95 mm (length of the packaging unit across the width of the product) and 50–170 nm (length of the packaging unit in the longitudinal direction of the product) in the case of a panty liner; and 60–200 mm in width and 60–300 mm in length in the case of an external packaging unit. The packaging units may, of course, be larger for accommodating larger napkins such as incontinence protectors and diapers.

According to another aspect of the invention, the packaging unit will include a moisture indicator that shows whether or not the packaging unit has retained its impermeability to moisture. Such a moisture indicator may comprise silica gel, such as silica gel 1–3 mm (manufacturer: Prolab, purchased from KeboLab, Art. No. 27661290), which changes colour when taking up moisture.

The packaging unit can be constructed in several ways, for instance by placing two films on one another and sealing the four open sides with respective joins or seams, by joining together a folded film with three joins or seams on the three open sides, by folding a "flow packed" film into two and joining the two open sides together with two joins and a join on the open upper side. A weld join or seam may have a width of about 20 mm. A few examples of packaging unit constructions will be evident from the following examples.

One aspect of the invention relates to a product packaging process which comprises (1) drying the absorbent article and applying the moisture-sensitive additive to the article either before or after drying said absorbent article, and (2) thereafter sealing the packaging unit containing said absorbent article to which said moisture-sensitive substance has been added.

It is important that the packaging unit and its contents are sufficiently dry when actually sealing said unit. This is ensured by drying the absorbent article in manufacture, either before or after applying the active additive.

When the active moisture-sensitive additive is comprised of lactobacilli, the additive can be applied in the form of a freeze-dried powder that contains lactobacilli, or in the form of a lactobacilli suspension. In this case, it is suitable to maintain the lowest possible water content or the highest possible concentration in the suspension in order not to introduce an unnecessary amount of water that must be later dried off. Lactobacilli will preferably be applied in an amount corresponding to $10^4$–$10^{12}$, preferably $10^6$–$10^{10}$ CFU/product (CFU: Colony Forming Unit).

When the moisture-sensitive additive is an odour-inhibitor of the zeolite type, the additive can be applied to the product in powder form. A suitable quantity/product has been found to be 0.5–1.5 g. The zeolite powder may be glued firmly to the absorbent material when said material is a roll material of the kind designated airlaid or LDA. The powder may alternatively be mixed in the cellulose pulp when forming a pulp mat although this is less suitable with respect to zeolites, because of the high moisture content involved in mat forming processes, about 10–12 percent by weight, and because the zeolite will then be able to take up water and thereby impair its odour-absorbing properties, as before mentioned.

It has also been found beneficial to dry the absorbent material in the form of roll material such as LDA or airlaid material, which is, known in the manufacture of napkins and panty liners. In this respect, it is suitable to dry the material to a water content below 1–2 percent by weight water. These materials can be dried at, e.g., 105° C. over one calendar day.

The atmosphere surrounding the applicator equipment shall be kept as dry as possible, as absorbent material readily absorbs moisture from the surroundings. It has been found suitable for the atmosphere to have a less than 20% humidity. The equipment may also be supplemented with an IR drier (IR oven MA 40, manufacturer: Sartorius, purchased from Tillqvist Analys) mounted on the machine when applying the moisture-sensitive additive.

A dry atmosphere can be ensured in the packaging unit, by delivering to said unit a dry gas, e.g. carbon dioxide, that has a highest water content of 5 ppm, prior to sealing the package.

Alternatively, the packaged product can be given a desired degree of dryness by adding a drying substance, a moisture absorbent, such as silica gel or zeolite, for instance.

A Flow Wrapper SP-2 manufacture by Flow Wrapper is an example of packaging machines that can be used to produce a moisture-tight package.

When cold sealing, up to about 1500 products/min. can be packaged with known technology.

The following examples are intended merely to describe the invention in further detail and shall not be considered as representing a limitation of the scope of the invention.

EXAMPLES

Example 1

Transport Conditions

Figure 1:
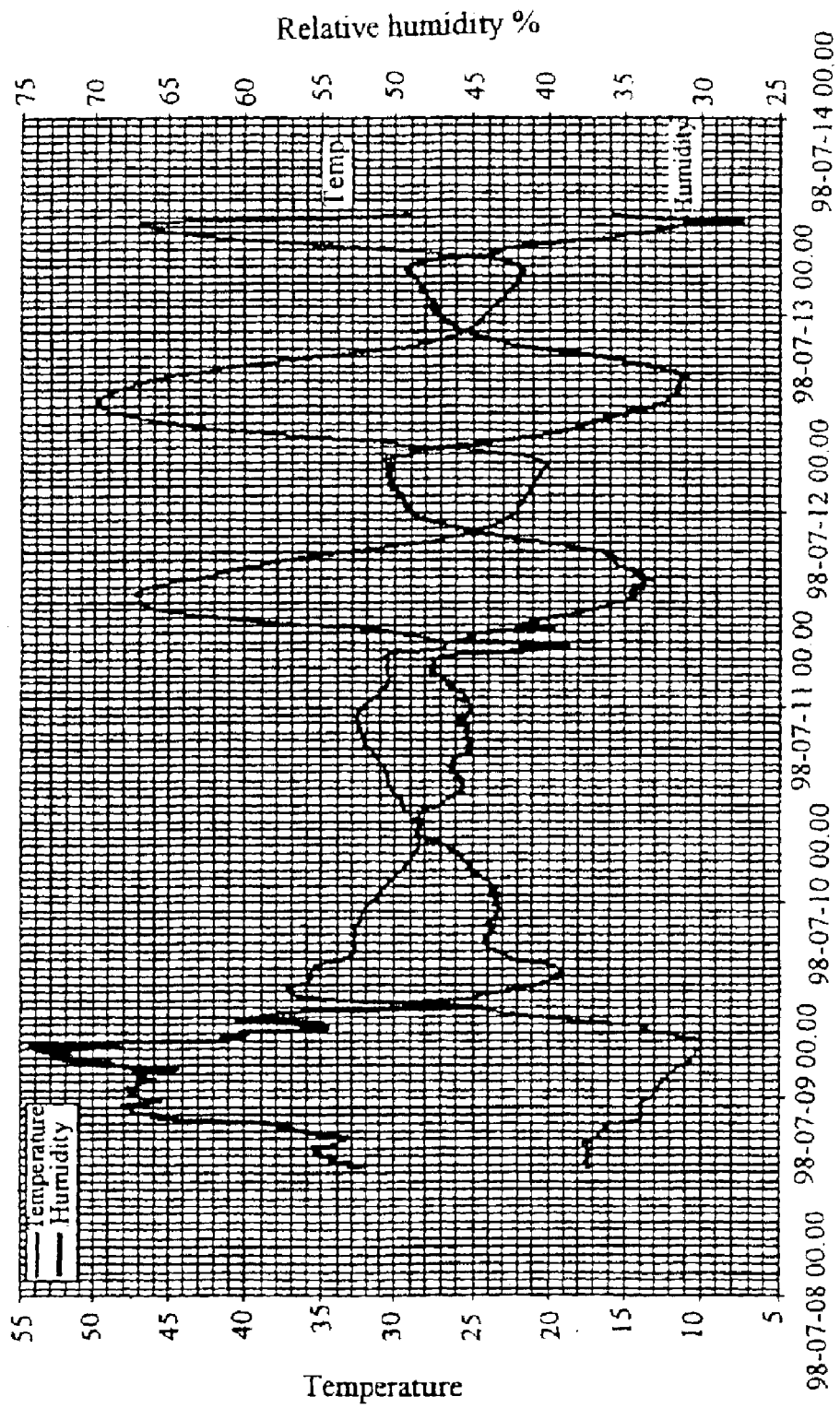
FIG. 1 shows temperature and air humidity when transporting sanitary products from Holland to Greece.

This example shows how temperature and air humidity vary in the storage space during transportation of sanitary products (FIG. 1) from Holland to Greece. The Figure shows that the relative humidity varies from 27–75% and the temperature varies from 1050° C.

Example 2

The affect of Moisture on the Lifetime of Lactobacilli

Figure 3:
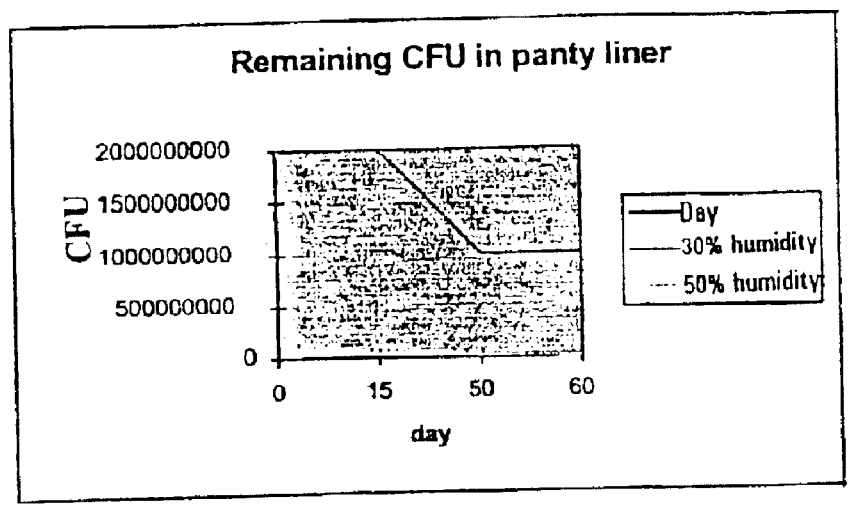
FIG. 3 is a curve illustrating the death of LB at room humidity 50% at 20° C. (schematically) as compared with room humidity of 30% at 20° C. applied to a panty liner in an unsealed bag of the mini-grip type.

FIG. 3 illustrates the survival time of lactobacilli that have been applied to a panty liner in a permeable minigrip-type bag in different humidity conditions (30% and 50% respectively). Lactobacilli quickly die in a normal climate (20° C., 50% relative humidity) (FIG. 3). These conditions correspond to a water content of an airlaid article material of about 4 percent by weight. The lactobacilli survive far better at a lower moisture content (20° C., 30% relative humidity) (FIG. 3). The airlaid material has a water content of about 3 percent by weight in this climate.

Example 3

Desiccant

The following working examples demonstrate the possibility of subsequently drying the material with the aid of a suitable desiccator. Commercially available panty liners retailed under the trademark Libresse were stored in a normal room climate of 20° C. and 44% humidity. The water content of the products was measured with a hygrometer that included IR elements (IR oven MA 40, manufacturer Sartorius, purchased from Tillqvist Analys) and found to be 4 percent by weight. The products were then packed singly in impervious aluminium bags together with two different types of desiccant, silica gel, so-called blue gel (silica gel 1–3 mm, Prolab, purchased from KeboLab, Art. No. 27661290) on the one hand and zeolite MOLSIV ADSORBENT type 13X in powder from United Oil Products on the other hand. Different quantities of powder were added, whereafter the samples were stored in a normal room climate (see above) for two calendar days. After two calendar days, the panty liners were taken out of the aluminium packages and the water content determined with the same apparatus as that mentioned above. It was found that the water content of the products had already fallen to about 1.5 percent by weight when adding 1 g powder/package. Higher quantities were not found to significantly lower the water content. The addition of the moisture absorbent powder to the package or to the product is thus an alternative method of achieving the desired dryness in order for the added lactobacilli to survive.

Example 4

Moisture Uptake in Odour Inhibitors

The following example is intended to demonstrate the effect of a sealed packaging unit with respect to a deodorising capacity. Panty liners were produced by joining together PE film, airlaid 105 g/m² and NW by means of hotmelt glue. 0.5 g of ABSCENTS 5000 was added to the product between the plastic backing sheet and the airlaid sheet. Subsequent to manufacture, half of the products were packed in impervious aluminum bags, which were welded together. The other half of the products were packed in conventional one-piece packages, which were open to the atmosphere on one side. The products were then stored in a climate room at a temperature of 20° C. and a humidity of 50% for six calendar days. The deodorising or odour-inhibiting capacity was determined after storage in the following way the products were removed from their respective packages and a 1.5 ml ammonia solution 0.2% was added to the products. The products were then placed in impervious plastic cans. A panel of six persons then carried out a sniff test after two hours. A can that contained a product, which had no zeolite or ammonia, was used as a reference. The cans were marked A=product stored in a conventional bag, B=reference with no ammonia odour, and C=product stored in impervious bags. The panel was asked to compare the samples in pairs and to indicate which sample had the strongest smell. The samples were then ranked from the strongest to the weakest smell. A unanimous verdict of ACB was given.

Example 5

Material WVTR

The WVTR of a number of materials was determined in the search for suitable material for use in accordance with the invention. The WVTR of these materials was determined with the aid of an apparatus designated LYSSY L 80-4000. The materials, their thicknesses and measured WVTR are shown in Table 1.

TABLE 1

Various materials and their WVTR (Water Vapour Transmission Rate).

| No. | Material | Manufacturer | Thickness ($\mu$m) | WVTR (g/m²/cal. Day) |
|---|---|---|---|---|
| 1 | Techbarrier H + PE + PET | Mitsubishi | 30 | 0.3 |
| 2 | VA 535670 (metallised PE/PET) | Nordenia | 30 | 0.3 |
| 3 | Techbarrier V + PE + PET | Mitsubishi | 30 | 0.7 |
| 4 | 4364 | Schur-Flexible | 85 | 1.3 |
| 5 | Coex HDPE Surlyn | Schur-Flexible | 50 | 1.7 |
| 6 | Coex Cheerios | Schur-Flexible | 60 | 2.6 |
| 7 | PET/PE |  | 60 | 4.9 |
| 8 | Libresse SW film | M&W | 40 | 9.7 |
| 9 | Libresse bag (cito) | M&W | 40 | 22 |

Example 6

Packaging Embodiments

Figure 2:
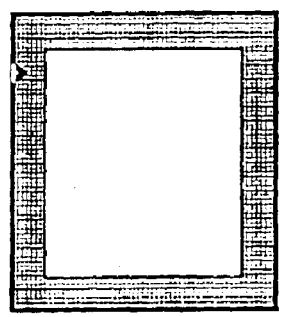
FIG. 2 illustrates examples of packaging processes, including joining, seaming and welding configurations (chequered surfaces).
Figure 2:
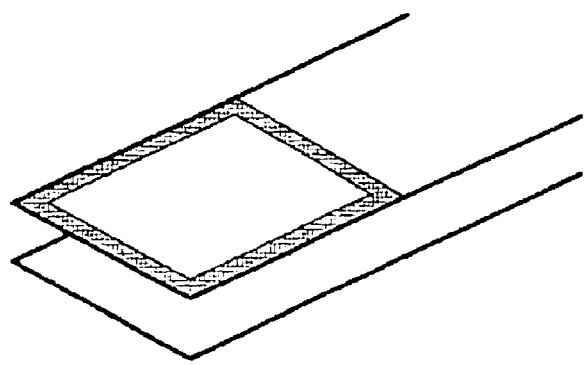
Figure 2:
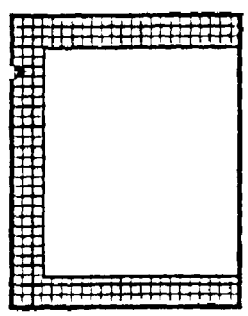
Figure 2:
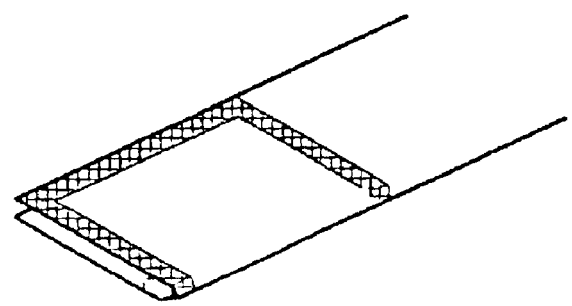
Figure 2:
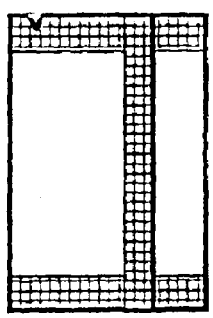
Figure 2:
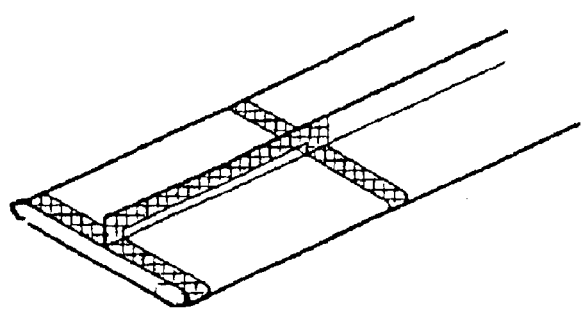

This example shows three options of constructing packages in accordance with the invention (FIG. 2).

What is claimed is:

1. A method of packaging an absorbent article selected from the group consisting of a sanitary napkin, a panty liner, a tampon, an incontinence protector, and a diaper, the absorbent article comprises one or more moisture-sensitive additives, the method comprising the steps of using at least one essentially impervious film material, the impervious film material being selected form the group consisting of PE (polyethylene), PP (polypropylene) PET (polyester), PA (polyamide), PETP, PVA (Polyvinyl alcohol), aluminum foil, aluminum oxide, and silicon oxide and the impervious film material having a highest WVTR (Water Vapour Transmission Rate) of 6 g/m²/calendar day in accordance with ASTME 398-83 in effect as of Jun. 9, 2000 to package the absorbent article, wherein the package is fully sealed with impervious joins or seams, wherein the pack comprises at least two material layers, of which one is an inner moisture barrier layer that is comprised of the at least one essentially impervious film.

2. The method according to claim 1, wherein the highest WVTR of the package is 4 g/m²/calendar day.

3. The method according to claim 1, wherein the highest WVTR of the package is 2 g/m²/calendar day.

4. The method according to claim 1, wherein the highest WVTR of the package is 1 g/m²/calendar day.

5. The method according to claim 1, wherein the package comprises a moisture indicator.

6. The method according to claim 1, wherein the package comprises a moisture absorbent.

7. The method according to claim 1, wherein the at least two layers comprise different materials.

8. The method according to claim 5, wherein the moisture indicator is a silica gel.

9. The method according to claim 1, wherein the moisture sensitive additive is an active additive.

10. A pack enclosing an absorbent article for absorption of bodily fluids, the absorbent article selected from the group consisting of a sanitary napkin, a panty liner, a tampon, an incontinence protector, and a diaper, wherein the absorbent article has at least one moisture-sensitive additive, the pack comprising at least one essentially impervious film material with impervious joins or seams, the impervious film material being selected from the group consisting of PE (polyethylene), PP (polypropylene), PET (polyester), PA (polyamide), PETP, PVA (Polyvinyl alcohol), aluminum foil, aluminum oxide, and silicon oxide and wherein the highest WVTR (Water Vapour Transmission Rate) of the pack is 6 $g/m^2$/calendar day in accordance with ASTME 398-83 in effect as of Jun. 9, 2000, wherein the sack comprises at least two material layers, of which one is an inner moisture barrier layer that is comprised of the at least one essentially impervious film.

11. The pack according to claim 10, wherein the highest WVTR of the pack is 4 $g/m^2$/calendar day.

12. The pack according to claim 10, wherein the highest WVTR of the pack is 2 $g/m^2$/calendar day.

13. The pack according to claim 10, wherein the highest WVTR of the pack is 1 $g/m^2$/calendar day.

14. The pack according to claim 10, wherein the package is fully sealed with the impervious joins or seams.

15. The pack according to claim 10, wherein the moisture sensitive additive is an active additive.

* * * * *